United States Patent
Kullik et al.

(10) Patent No.: US 11,977,063 B2
(45) Date of Patent: May 7, 2024

(54) SENSOR MODULE FOR RESPIRABLE GAS MIXTURES, VENTILATOR, THERAPY DEVICE AND METHOD FOR MEASURING A PLURALITY OF GASES OF A RESPIRABLE GAS MIXTURE

(71) Applicant: Drägerwerk AG & Co. KGaA, Lübeck (DE)

(72) Inventors: Götz Kullik, Lübeck (DE); Peter Dreyer, Pansdorf (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 724 days.

(21) Appl. No.: 16/591,185

(22) Filed: Oct. 2, 2019

(65) Prior Publication Data
US 2020/0033310 A1    Jan. 30, 2020

Related U.S. Application Data

(63) Continuation of application No. 14/946,101, filed on Nov. 19, 2015, now abandoned.

(30) Foreign Application Priority Data

Nov. 28, 2014   (DE) ..................... 10 2014 017 619.3

(51) Int. Cl.
*A61M 16/00* (2006.01)
*A61M 16/10* (2006.01)
(Continued)

(52) U.S. Cl.
CPC ....... *G01N 33/0031* (2013.01); *A61M 16/104* (2013.01); *A61M 16/12* (2013.01);
(Continued)

(58) Field of Classification Search
CPC ................ A61M 16/104; A61M 16/12; A61M 2016/1025; A61M 2016/103;
(Continued)

(56) References Cited

U.S. PATENT DOCUMENTS

| 5,910,765 A | 6/1999 | Slemon et al. |
| 6,430,987 B1 * | 8/2002 | Stark ....................... G01N 27/74 73/25.02 |

(Continued)

FOREIGN PATENT DOCUMENTS

| CN | 101608927 A | 12/2009 |
| DE | 19720007 A1 | 11/1998 |

(Continued)

*Primary Examiner* — Margaret M Luarca
*Assistant Examiner* — Sarah B Lederer
(74) *Attorney, Agent, or Firm* — McGlew and Tuttle, P.C.

(57) ABSTRACT

A respirable gas mixture sensor module (10) includes a first sensor (1, 14-1, 14-2) for measuring a gas and a second sensor (18, 18-1, 18-2) for measuring the same gas and apply different principles of measurement. The sensor module (10) is configured to determine a measurement result for the gas taking into account the measurements. As an alternative the sensor module (10) includes a first sensor group (12) including a first sensor (14, 14-1, 14-2) and a second sensor group (16) including a second sensor (18, 18-1, 18-2), each for measuring both a first and a second gas and apply different principles of measurement. The sensor module is configured to determine measurement results for the gases, taking into account the respective measurements of the first and second sensors. A ventilator, a therapy device and a method for measuring a plurality of gases of a respirable gas mixture are also provided.

20 Claims, 3 Drawing Sheets

(51) Int. Cl.
  *A61M 16/12* (2006.01)
  *G01N 33/00* (2006.01)
(52) U.S. Cl.
  CPC .............. *A61M 2016/1025* (2013.01); *A61M 2016/103* (2013.01); *A61M 2205/3306* (2013.01); *A61M 2205/3368* (2013.01)
(58) Field of Classification Search
  CPC .. A61M 2205/3306; A61M 2205/3368; G01N 33/0031
  See application file for complete search history.

(56) References Cited

U.S. PATENT DOCUMENTS

| | | | |
|---|---|---|---|
| 2002/0029003 A1 | 3/2002 | Mace et al. | |
| 2002/0152037 A1* | 10/2002 | Sunshine | G01N 29/022 702/23 |
| 2004/0227087 A1 | 11/2004 | Markham et al. | |
| 2008/0004004 A1 | 1/2008 | Wu et al. | |
| 2009/0312984 A1 | 12/2009 | Delajoud et al. | |
| 2012/0312302 A1* | 12/2012 | Cardelius | A61M 16/12 128/203.14 |
| 2013/0211207 A1* | 8/2013 | Joseph | A61M 16/01 600/301 |
| 2016/0001001 A1 | 1/2016 | Wruck et al. | |
| 2016/0025529 A1 | 1/2016 | Astegher et al. | |

FOREIGN PATENT DOCUMENTS

| | | | | |
|---|---|---|---|---|
| DE | 10164313 | A1 | 7/2003 | |
| DE | 102004044142 | B3 | 6/2006 | |
| DE | 102011089064 | A1 | 6/2013 | |
| DE | 102013002408 | A1 | 8/2014 | |
| DE | 202014103355 | U1 | 8/2014 | |
| WO | 03055552 | A1 | 7/2003 | |
| WO | WO-2009058083 | A1 * | 5/2009 | .......... A61M 16/085 |

* cited by examiner

SENSOR MODULE FOR RESPIRABLE GAS MIXTURES, VENTILATOR, THERAPY DEVICE AND METHOD FOR MEASURING A PLURALITY OF GASES OF A RESPIRABLE GAS MIXTURE

CROSS REFERENCE TO RELATED APPLICATIONS

This application claims the benefit of priority under 35 U.S.C. § 120 of U.S. patent application Ser. No. 14/946,101 filed Nov. 19, 2015, which claims the benefit of priority under 35 U.S.C. § 119 of German Patent Application 10 2014 017 619.3 filed Nov. 28, 2014, the entire contents of which are incorporated herein by reference.

FIELD OF THE INVENTION

The present invention pertains to sensor modules for respirable gas mixtures, ventilators (also known as ventilators), therapy devices and to a method for measuring a plurality of gases of a respirable gas mixture.

BACKGROUND OF THE INVENTION

Sensor modules for respirable gas mixtures are intended, for example, for medical applications in ventilators or therapy devices for measuring gas concentrations in the breathing air. Furthermore, sensor modules for respirable gas mixtures for safety-related applications are known, in which, for example, measurements of the concentrations of certain gases in chemical industrial plants are carried out.

Such sensor modules, which have a sensor for measuring a certain gas of the respirable gas mixture, are known. For example, optical absorption sensors or electrochemical sensors are known for this.

A paramagnetic thermal sensor for measuring a concentration of oxygen is, furthermore, known from DE 10 2011 018 670 A1.

SUMMARY OF THE INVENTION

An object of the present invention is to provide a sensor module for respirable gas mixtures, which makes possible an improved functionality, availability and safety of the sensor module, as well as a corresponding ventilator, therapy device and a corresponding method for measuring a plurality of gases of a respirable gas mixture.

A sensor module according to the present invention for respirable gas mixtures comprises at least one first sensor for measuring a gas and at least one second sensor for measuring the same gas, wherein the first sensor for measuring the gas and the second sensor for measuring the gas apply different principles of measurement. The sensor module is configured to determine a measurement result for the gas taking into account the measurements of the first sensor for measuring the gas and of the second sensor for measuring the gas (the measurement result is a function of the measurements of the first sensor for measuring the gas and a function of the second sensor for measuring the gas). A redundancy is obtained in this way in the measurement of the gases. Furthermore, it is possible to increase the accuracy of the measurement or the availability of the measuring system by multiple measurements of a gas.

A sensor module according to the present invention for respirable gas mixtures especially advantageously comprises a first sensor group, which has at least one first sensor for measuring a first gas and a second gas, and a second sensor group, which has at least one second sensor for measuring the first gas and the second gas. The first sensor for measuring the first gas and the second sensor for measuring the first gas apply different principles of measurement, and the first sensor for measuring the second gas and the second sensor for measuring the second gas apply different principles of measurement. The sensor module is configured to determine a measurement result for the first gas taking into account (as a function of) the measurements of the first sensor for measuring the first gas and of the second sensor for measuring the first gas, and to determine a measurement result for the second gas taking into account (as a function of) the measurements of the first sensor for measuring the second gas and of the second sensor for measuring the second gas. A redundancy is obtained in this way in the measurement of the gases. It is, furthermore, possible by multiple measurements of a gas to increase the accuracy of the measurement or to increase the availability of the measuring system.

According to a preferred embodiment, at least one first sensor and/or at least one second sensor is an optical absorption sensor. Optical absorption sensors are especially suitable for measuring a $CO_2$ concentration or certain organic substances, for example, anesthetic gases.

The first and/or second sensors may have, for example, a plurality of optical absorption sensors, the principles of measurement of the plurality of optical absorption sensors differ by different wavelength ranges.

At least one first sensor and/or at least one second sensor may be a paramagnetic thermal sensor. Such sensors make it possible, for example, to measure oxygen, $CO_2$ and/or anesthetic gases.

At least one first sensor and/or at least one second sensor may be an electrochemical sensor. This makes it possible, for example, to measure an oxygen concentration.

According to another embodiment of the present invention, a third sensor group may be provided, which has at least one third sensor for measuring the first and/or second gas, wherein the third sensor for measuring the first and/or second gas applies the same principle of measurement as at least one of the first and/or second sensors. A three-channel application can be achieved in this way for critical measured values.

The first gas is preferably oxygen and the second gas is carbon dioxide and/or an anesthetic gas. The sensor module can be used in this way in ventilators and especially anesthesia apparatuses.

The sensor module may be configured to determine the measurement result for the first and/or second gas by a measurement result of a measurement of the respective gas being determined with the first sensor or with the second sensor and by a plausibility check being performed by means of a measurement result of a measurement of the same gas by a sensor having a different principle of measurement, and/or by a plausibility check being performed by means of a measurement result of a measurement of another gas by another sensor. The two measurement results can be checked for consistency in this way and an error in the sensor module can be detected. When an error is detected, an emergency operation, which increases the availability of the sensor module, can be provided.

At least one of the first and/or second sensors is configured to measure both the first gas and the second gas with a common principle of measurement. The number of individual sensors can be reduced in this way. Furthermore, cross sensitivities of the sensors can be productively utilized in this way.

The present invention pertains, furthermore, to a ventilator and especially to an anesthesia apparatus having an above-described sensor module.

Furthermore, the present invention provides a therapy device with such a ventilator and with a dispensing device. The dispensing device is configured to dispense a quantity of active ingredient as a function of measurement result of the sensor module.

A method according to the present invention for measuring a gas of a respirable gas mixture comprises the method steps of measuring this gas by means of at least two sensors having different principles of measurement and of determining a measurement result for this gas taking into account (as a function of) the measurements of the at least two sensors having different principles of measurement. Such a measuring method makes possible a redundancy in the measurement and thus increases the reliability and the availability of a correspondingly operated sensor module.

According to a preferred variant of the method, a first gas is measured by means of at least two sensors having different principles of measurement, and a second gas is measured by means of at least two sensors having different principles of measurement. A measurement result for the first gas is determined taking into account (as a function of) the measurements of the at least two sensors having different principles of measurement, and a measurement result for the second gas is determined taking into account (as a function of) the measurements of the at least two sensors having different principles of measurement.

The determination of the measurement result for the first and/or second gas preferably comprises the determination of a measurement result by means of the first or second principle of measurement and a plausibility check by means of a measurement result of a measurement of the same gas with a different principle of measurement, and/or a plausibility check by means of a measurement result of a measurement of another gas with a different principle of measurement.

Further advantages and features of the present invention appear from the following description and from the drawings, to which reference is made. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
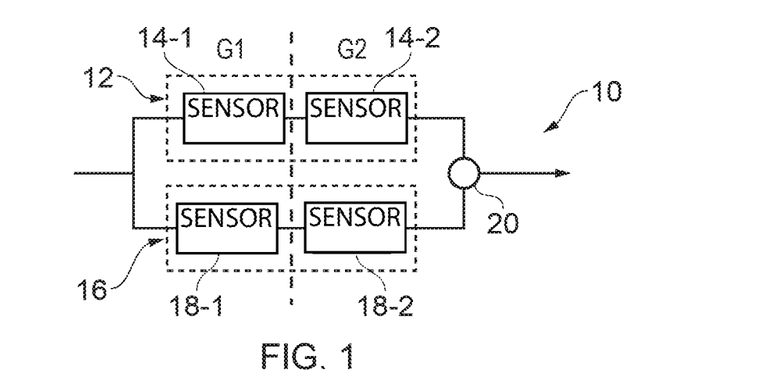
FIG. 1 is a schematic view of a sensor module according to a first embodiment of the present invention.

Referring to the drawings, FIG. 1 shows a first embodiment of a sensor module 10 for respirable gas mixtures. The sensor module 10 comprises a first sensor group 12, which has at least one first sensor 14 for measuring a first gas G1 and a second gas G2, and a second sensor group 16, which has at least one second sensor 18 for measuring the first gas G1 and the second gas G2. Two first sensors 14-1 and 14-2 and two second sensors 18-1 and 18-2 are provided in the first embodiment.

The first sensor 14-1 for measuring the first gas G1 and the second sensor 18-1 for measuring the first gas G1 are configured each such that they apply different principles of measurement for measuring the first gas G1.

The first sensor 14-2 for measuring the second gas G2 and the second sensor 18-2 for measuring the second gas G2 are correspondingly configured to apply each different principles of measurement.

The different principles of measurement may be, for example, optical gas measurement sensors, paramagnetic gas measurement sensors, electrochemical gas measurement sensors or heat conduction gas measurement sensors. Optical absorption sensors are especially suitable for measuring a $CO_2$ concentration or certain organic substances, for example, anesthetic gases.

The principles of measurement in optical absorption sensors may also differ for this invention due to different wavelength ranges, where a measurement in a second and different wavelength makes it possible to measure the concentration of one gas using different principles of measurement as to obtain redundancy.

A paramagnetic thermal sensor may be, for example, another principle of measurement. Such sensors make it possible to measure, for example, oxygen, $CO_2$ and/or anesthetic gases.

An electrochemical sensor may be another principle of measurement. This makes it possible, for example, to measure an oxygen concentration.

Figure 3:
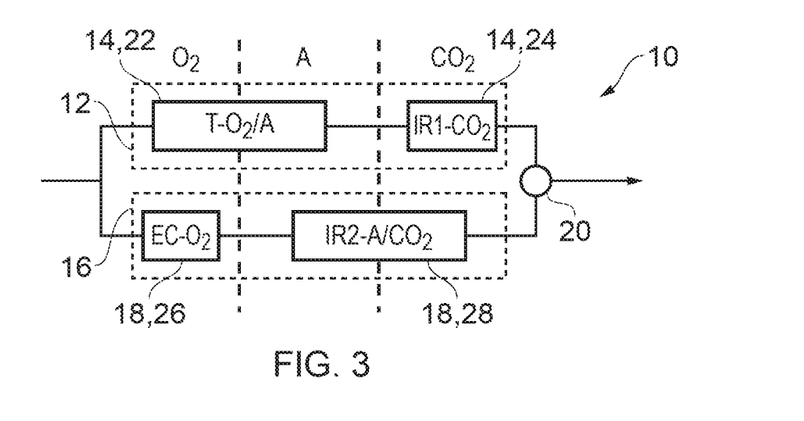
FIG. 3 is a schematic view of a sensor module according to a third embodiment of the present invention.
Figure 4:
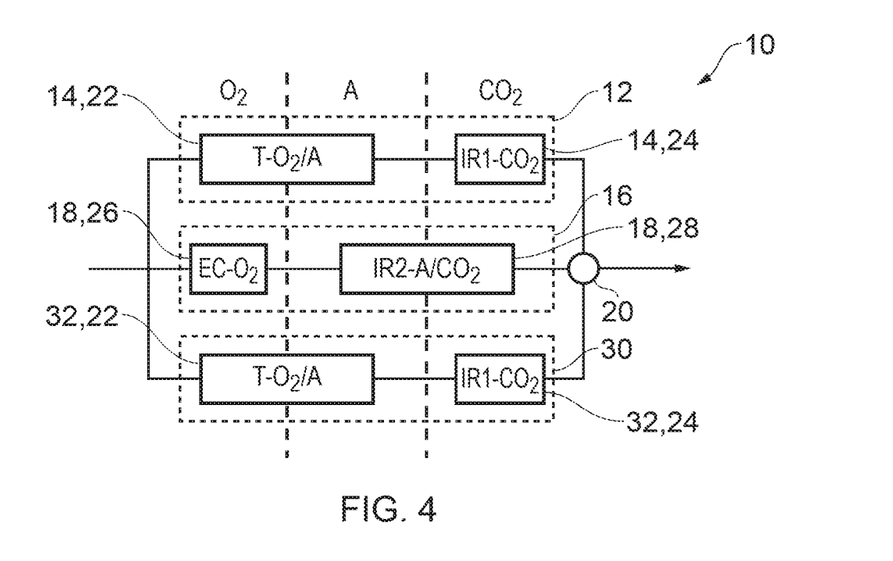
FIG. 4 is a schematic view of a sensor module according to a fourth embodiment of the present invention.
Figure 5:
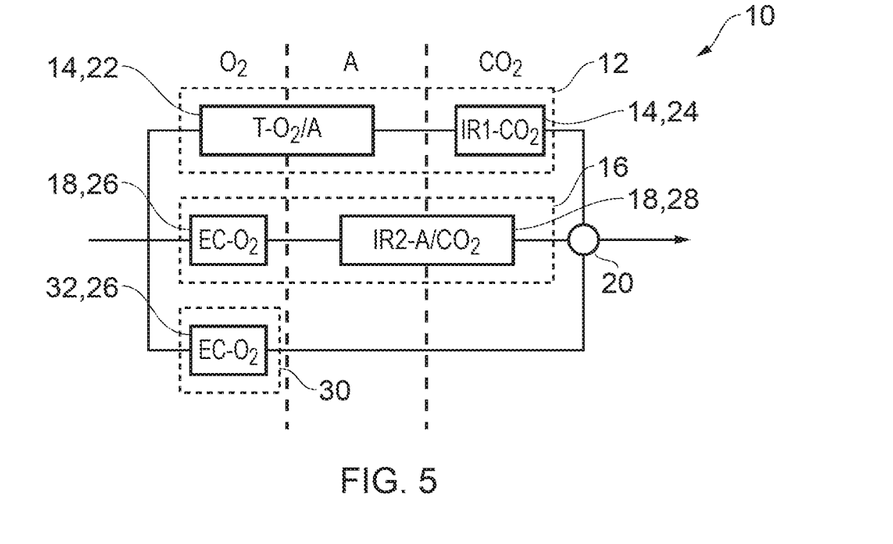
FIG. 5 is a schematic view of a sensor module according to a fifth embodiment of the present invention.

Advantageous combinations of sensors having different principles of measurement are shown in the embodiments shown in FIGS. 3 through 5.

The sensor module 10 comprises, furthermore, an analysis unit 20, which is configured to determine a measurement result for a first gas G1 taking into account the measurements of the first sensor 14-1 for measuring the first gas G1 and of the second sensor 18-1 for measuring the first gas G1, and to determine measurement result for the second gas G2 taking into account the measurements of the first sensor 14-2 for measuring the second gas G2 and of the second sensor 18-2 for measuring the second gas G2. A redundancy is obtained in this way in the measurement of the gases G1 and G2. Furthermore, it is possible to increase the accuracy of the measurement or the availability of the measuring system by the multiple measurements of a gas.

The analysis unit 20 of the sensor module 10 is configured in the embodiment being shown such that the measurement result for the first and second gases is determined by determining a measurement result of a measurement of the respective gas with the first sensor 14 or with the second sensor 18 and by carrying out a plausibility check by means of a measurement result of a measurement of the same gas by a sensor having a different principle of measurement. The two measurement results can be checked for consistency in this manner, and an error in the sensor module can be detected. When an error is detected, an emergency operation, which increases the availability of the sensor module, can be provided.

It is possible, as an alternative or in addition, that a plausibility check is carried out by means of a measurement result of a measurement of another gas by another sensor. The different measurement results can be checked for plausibility in this way, for example, by setting up the balance of the different gas components in case of known breathing gas mixture components.

It is also possible that the sensor module 10 is configured only to measure a gas G1 and the sensor module 10 correspondingly has a first sensor 14-1 and a second sensor 18-1, which apply different principles of measurement, and the analysis unit 20 is configured to determine a measurement result for the gas G1 taking into account the measurements of the at least two sensors having different principles of measurement. Such an arrangement corresponds essentially to the left half of the sensor module 10 from FIG. 1. For example, an electrochemical sensor and a paramagnetic thermal sensor may be provided for measuring oxygen in a respirable gas mixture.

Figure 2:
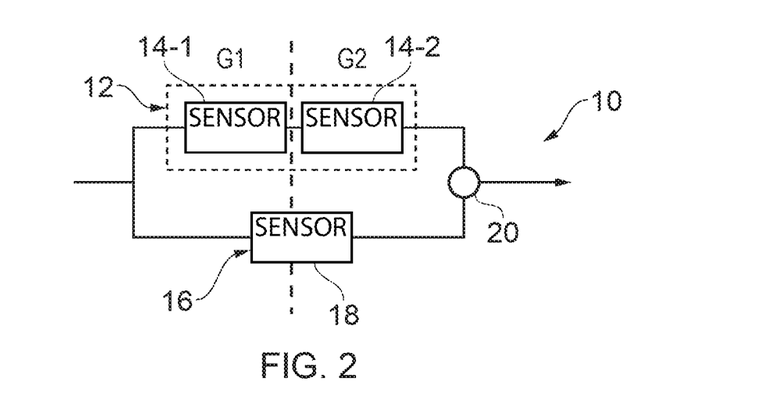
FIG. 2 is a schematic view of a sensor module according to a second embodiment of the present invention.

FIG. 2 shows a second embodiment of a sensor module 10 that again comprises a first sensor group 12, which has at least one first sensor 14 for measuring a first gas G1 and a second gas G2 (particularly a first sensor 14-1 for measuring the first gas G1 and another first sensor 14-2 for measuring the second gas G2). The second embodiment of a sensor module 10 further comprises a second sensor group 16 that has only a common second sensor 18, which is configured to measure both the first gas and the second gas with a common principle of measurement. The number of individual sensors is reduced in this way and a simple and cost-effective design of the sensor module 10 is made possible.

The common second sensor 18 is configured, for example, for measuring the first gas in the second embodiment being shown, and the common second sensor 18 has a cross sensitivity to the second gas. The cross sensitivity would have to filtered out of the measurement results in case of a conventional operation of the sensor 18. The cross sensitivity can be used in the second embodiment being shown to obtain an independent measurement result for the second gas. In a first step of the analysis, the measurement results can be checked for plausibility with the independent measurement results of the first sensors 14-1 and 14-2, which were each measured according to different principles of measurement, and, for example, a check as to whether the respective measurement results agree within their error limits/tolerance/accuracy/margin of error. The measurement results of the first sensors 14-1, 14-2 can then be used in a second step to improve the accuracy of the measurement, for example, by an improved determination of the cross sensitivity. A cross sensitivity of a sensor 18 can be used productively in this way.

Figure 6:
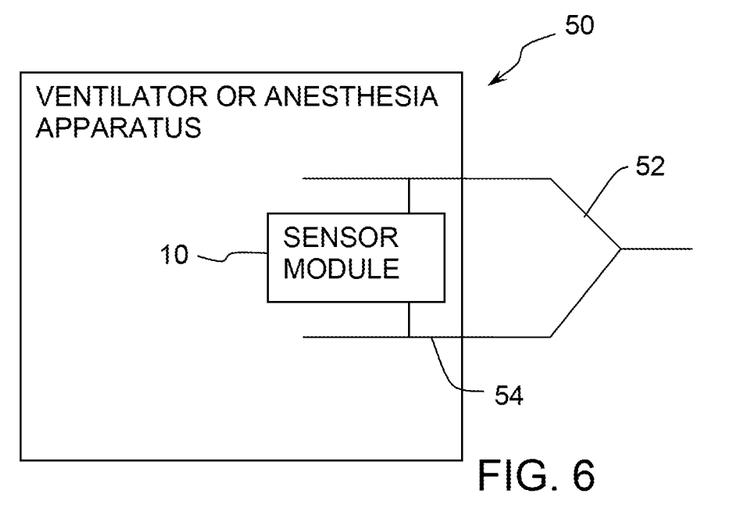
FIG. 6 is a schematic view of a ventilator or anesthesia apparatus with a sensor module according to any of the sensor module embodiments of the present invention.

FIG. 3 shows a concrete embodiment for measuring three gas components of a respirable gas mixture, wherein $O_2$ is measured as the first gas, an anesthetic gas A is measured as a second gas, and carbon dioxide, $CO_2$, is measured as the third gas. Such a sensor module 10 may be used especially in ventilators, and anesthesia apparatuses (such as a ventilator or anesthesia apparatus 50—FIG. 6).

Figure 7:
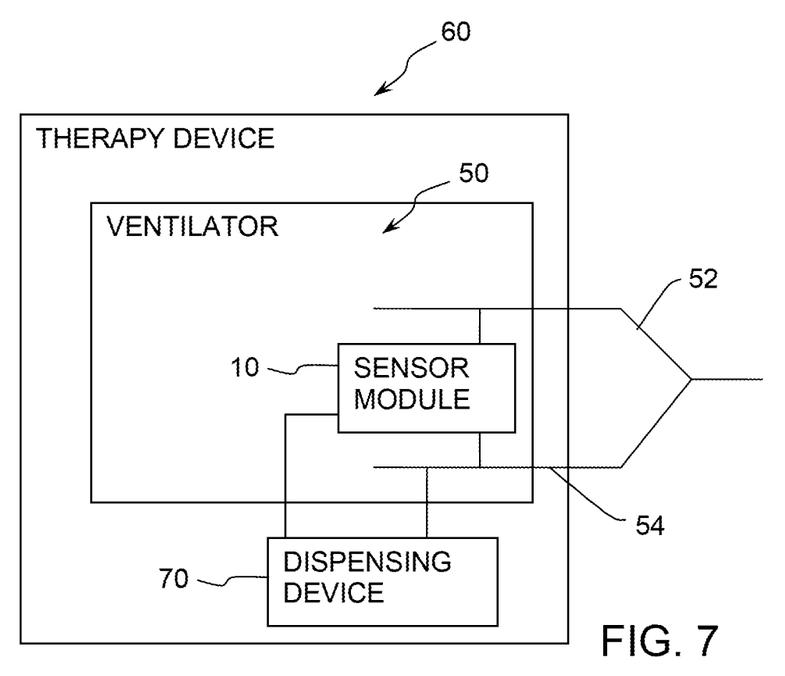
FIG. 7 is a schematic view of therapy device with a ventilator, an active ingredient dispensing device and with a sensor module according to any of the sensor module embodiments of the present invention.

Furthermore, such a sensor module 10 may be used in a therapy device 60, which comprises a ventilator 50 and a dispensing device 70 (FIG. 7). The dispensing device 70 is configured to dispense a quantity of active ingredient as a function of a measurement result of the sensor module 10.

The first sensor group 12 has a paramagnetic thermal sensor 22 and a first infrared absorption sensor 24 as first sensors 14. The paramagnetic thermal sensor 22 makes it possible to measure oxygen and anesthetic gases (cross sensitivities). The first infrared absorption sensor 24 is configured such that it is designed to measure absorption in a first wavelength range, in which a measurement of a $CO_2$ concentration is possible.

The second sensor group 16 has an electrochemical sensor 26 and a second infrared absorption sensor 28 as second sensors 18. The electrochemical sensor 26 is configured to measure an oxygen concentration. The second infrared absorption sensor 28 is configured to measure absorption in a second wavelength range, wherein the second wavelength range differs from the first wavelength range of the first infrared absorption sensor 24, and the measurement in the different second wavelength range makes it possible to measure the concentration of an anesthetic gas and a $CO_2$ concentration (cross sensitivities).

Analogously to the first and second embodiments, the different measurements carried out according to different principles of measurement can be used for mutual plausibility checking. Further, the measurements by the sensors 24 and 26 may be used, for example, to improve the measurements by the common sensors 22, 28 in respect to the measurement of anesthetic gas A.

FIGS. 4 and 5 show each another embodiment, in which a third sensor group 30 is provided, which has at least one third sensor 32 for measuring the first and/or second gas, the third sensor 32 applying the same principle of measurement for measuring the first and/or second gas as at least one of the first and/or second sensors 14, 18. A three-channel arrangement is obtained in this way for critical measured values.

In the embodiment shown in FIG. 4, the third sensor group 30 comprises a paramagnetic thermal sensor 22 and a first infrared absorption sensor 24 as third sensors 32. The paramagnetic thermal sensor 22 makes it possible to measure oxygen and anesthetic gases. The first infrared absorption sensor 24 is configured such that it is configured for the measurement of absorption in a first wavelength range in which a measurement of a $CO_2$ concentration is possible. The design of the third sensor group is thus identical in the embodiment being shown to that of the first sensor group 12. However, the respective sensors may also differ in terms of their mode of construction, the manufacturer and/or a production series in order to avoid systematic errors in case of sensors having an identical design and/or configuration. All three components of the gas mixture are measured in a three-channel measurement in this embodiment of the sensor module 10. Four different principles of measurement are applied.

In the embodiment shown in FIG. 5, the third sensor group 30 comprises only an electrochemical sensor 26. A three-channel measurement is thus provided for the most important component of the gas mixture, oxygen, while a two-channel measurement is provided for the anesthetic gas and $CO_2$. An evaluation of the heat conduction and the paramagnetic lock-in signals may be performed for anesthetic gas and $CO_2$ for considering redundancy. By evaluating the oxygen concentration provided by the electrochemical oxygen sensor with the paramagnetically measured lock-in signal and the heat conduction values associated therewith, information can be obtained on the reliability of the measurement based on the plausibility consideration. The comparison of the measured parameters of the thermal measuring head, of the paramagnetically measured lock-in signal and of an electrochemically measured oxygen signal and the deviation of these parameters within defined thresholds makes it possible to obtain information on whether there is an external system error, for example, infiltrated gas or pressure surge, an internal failure within the module, for example, in the heat conduction sensor, magnetic system, electronics or hardware.

It is, furthermore, possible to carry out a plausibility check for $CO_2$ by setting up the balance of the concentrations of the exhalation phase with the inhalation phase (e.g., by measuring the exhalation gas in exhalation line 52 and inhalation gas in inhalation line 54). Since the gas mixture is usually that of oxygen, nitrogen and $CO_2$ in ventilators with mask breathing, not only can the metabolic parameter of the patient be displayed, but the dispensing of oxygen is additionally also monitored by measuring a second component, e.g., oxygen.

A method for measuring a plurality of gases of a respirable gas mixture will be described below on the basis of the sensor module 10 in FIG. 1. The method comprises the method steps of measuring a first gas by means of at least two sensors 14-1, 18-1 having different principles of measurement and of measuring a second gas by means of at least two sensors 14-2, 18-2 having different principles of measurement.

A measurement result for the first gas G1 is determined with different principles of measurement, taking into account the measurements of the at least two sensors 14-1, 18-1, and a measurement result for the second gas is determined taking into account the measurements of the at least two sensors 14-2, 18-2 having different principles of measurement.

The determination of the measurement result for the first and/or second gas comprises the determination of a measurement result by means of the first or second principle of measurement and a plausibility check by means of a measurement result of a measurement of the same gas with a different principle of measurement, and/or a plausibility check by means of a measurement result of a measurement of another gas with a different principle of measurement.

Further alternatives of the measuring method appear from the features of the other embodiments according to FIG. 2 to FIG. 5.

While specific embodiments of the invention have been shown and described in detail to illustrate the application of the principles of the invention, it will be understood that the invention may be embodied otherwise without departing from such principles.

APPENDIX

List Of Reference Numbers

10 Sensor module
12 First sensor group
14 First sensor
16 Second sensor group
18 Second sensor
20 Analysis unit
22 Paramagnetic thermal sensor
24 First infrared absorption sensor
26 Electrochemical sensor
28 Second infrared absorption sensor
30 Third sensor group
32 Third sensor

What is claimed is:

1. A sensor module for respirable gas mixtures, the sensor module comprising:
   a first sensor for measuring a first gas and a second gas with first measurement characteristics, said first sensor having error limits, the first measurement characteristics having a first sensitivity to the first gas and having a second sensitivity to the second gas;
   a second sensor for measuring the first and second gas with second measurement characteristics, wherein said first measurement characteristics are different from said second measurement characteristics, said second sensor having error limits, the second measurement characteristics having a first sensitivity to the first gas and having a second sensitivity to the second gas; and
   an analysis unit configured to determine a gas measurement result of the first gas as a function of measurements of said first sensor and as a function of measurements of said second sensor, said analysis unit also being configured to determine a gas measurement result of the second gas as a function of the measurements of said first sensor and as a function of the measurements of said second sensor;
   said analysis unit performing a plausibility check of the gas measurement results by determining if the respective gas measurement results obtained from the different measurement characteristics agree within their respective error limits.

2. The sensor module for respirable gas mixtures in accordance with claim 1, further comprising:
   another first sensor for measuring the first gas and the second gas with the first measurement characteristics, said another first sensor having error limits, said first sensor and said another first sensor forming a first sensor group;
   another second sensor for measuring the first gas and the second gas with the second measurement characteristics, said another second sensor having error limits, said second sensor and said another second sensor forming a second sensor group for measuring the first gas and the second gas;
   said analysis unit performing the plausibility check of the gas measurement results of said first and second sensor groups by determining if the respective gas measurement results agree within their respective error limits.

3. The sensor module in accordance with claim 1, wherein;
   said first sensor and said second sensor is an optical absorption sensor.

4. The sensor module in accordance with claim 3, wherein:
   said first sensor is an optical absorption sensor with a first sensor gas-specific wavelength range, and said second sensor is an optical absorption sensor with a second sensor gas-specific wavelength range;
   the first measurement characteristics differ from the second measurement characteristics by the first sensor gas-specific wavelength range being differing from the second sensor gas-specific wavelength range.

5. The sensor module in accordance with claim 1, wherein;

one of said first sensor and said second sensor is a paramagnetic thermal sensor.

6. The sensor module in accordance with claim 1, wherein:
one said first sensor and said second sensor is an electrochemical sensor.

7. The sensor module in accordance with claim 2, further comprising:
a third sensor group comprising a third sensor for measuring at least one of the first and the second gas, wherein said third sensor applies a same measurement characteristic as at least one of the sensors with said first sensor group and with said second sensor group.

8. The sensor module in accordance with claim 1, wherein:
the first gas is oxygen and the second gas is at least one of carbon dioxide and an anesthetic gas.

9. The sensor module in accordance with claim 1, wherein:
said analysis unit performs the plausibility check by at least one of:
determining a measurement result of a measurement of the same gas by said sensors having different measurement characteristics; and
determining a measurement result of a measurement of another gas by the other of said first sensor and the second sensor.

10. The sensor module in accordance with claim 1, wherein:
at least one of said first sensor and said second sensor is configured to measure both the first gas and the second gas with common measurement characteristics.

11. A ventilator or anesthesia apparatus providing a respirable gas mixture to a patient, the apparatus comprising:
an inhalation line configured to supply the respirable gas mixture to the patient;
a sensor module configured to receive the respirable gas mixture, the sensor module comprising:
a first sensor for measuring a first gas and a second gas with first measurement characteristics, the first sensor having a tolerance, the first measurement characteristics having a first sensitivity to the first gas and having a second sensitivity to the second gas;
a second sensor for measuring the first and second gas with second measurement characteristics, wherein the first measurement characteristics are different from the second measurement characteristics, the second sensor having a tolerance, the second measurement characteristics having a first sensitivity to the first gas and having a second sensitivity to the second gas; and
an analysis unit configured to determine a gas measurement result of the first gas as a function of measurements of the first sensor and as a function of measurements of the second sensor, the analysis unit also being configured to determine a gas measurement result of the second gas as a function of the measurements of the first sensor and as a function of the measurements of the second sensor;
the analysis unit performing a plausibility check of the gas measurement results by determining if the respective gas measurement results obtained from the different measurement characteristics are within their respective tolerances.

12. The apparatus in accordance with claim 11 in combination with a dispensing device to form a therapy device, the dispensing device being configured to dispense a quantity of active ingredient as a function of a measurement result of the sensor module.

13. The apparatus in accordance with claim 12, wherein at least one the first sensor and the second sensor is an optical absorption sensor.

14. The apparatus in accordance with claim 13, wherein the first sensor is an optical absorption sensor with a first sensor gas-specific wavelength range, and the second sensor is an optical absorption sensor with a second sensor gas-specific wavelength range and the measurement characteristics differ from the second measurement characteristics by the first sensor gas-specific wavelength range being differing from the second sensor gas-specific wavelength range.

15. The apparatus in accordance with claim 12, wherein one of the first sensor and the second sensor is a paramagnetic thermal sensor.

16. The apparatus in accordance with claim 12, wherein the first sensor and the second sensor is an electrochemical sensor.

17. A method for measuring at least one gas of a respirable gas mixture, the method comprising the steps of:
providing a first sensor for measuring a first gas and a second gas with first measurement characteristics, the first sensor having error limits, the first measurement characteristics having a first sensitivity to the first gas and having a second sensitivity to the second gas;
providing a second sensor for measuring the first and second gas with second measurement characteristics, wherein said first measurement characteristics are different from said second measurement characteristics, the second sensor having error limits, the second measurement characteristics having a first sensitivity to the first gas and having a second sensitivity to the second gas;
determining a gas measurement result of the first gas as a function of measurements of the first sensor and as a function of measurements of the second sensor;
determining a gas measurement result of the second gas as a function of the measurements of the first sensor and as a function of the measurements of the second sensor;
performing a plausibility check of the gas measurement results by determining if the respective gas measurement results obtained from the different measurement characteristics agree within their respective error limits.

18. The method in accordance with claim 17, further comprising:
measuring another gas with the first sensor and the second sensor having different measurement characteristics; and
determining a measurement result, for the another gas, as a function of the measurements of the first sensor and the second sensor having different measurement characteristics.

19. The method in accordance with claim 17, wherein;
said performing of the plausibility check is performed by at least one of:
determining a measurement result of a measurement of the same gas by the sensors having measurement characteristics; and
determining a measurement result of a measurement of another gas by the other of the first sensor and the second sensor.

20. The method in accordance with claim 17, further comprising:
providing another first sensor for measuring the first gas and the second gas with the first measurement characteristics, said another first sensor having error limits, said first sensor and said another first sensor forming a first sensor group;

providing another second sensor for measuring the first gas and the second gas with the second measurement characteristics, said another second sensor having error limits, said second sensor and said another second sensor forming a second sensor group for measuring the first gas and the second gas;

performing a plausibility check of the gas measurement results of said first and second sensor groups by determining if the respective gas measurement results agree within their respective error limits.

* * * * *